United States Patent [19]

Kuhrts et al.

[11] Patent Number: 5,993,860
[45] Date of Patent: Nov. 30, 1999

[54] NSADI DELIVERY EMPLOYING A POWDERED HYDROCOLLOID GUM OBTAINABLE FROM HIGHER PLANTS

[75] Inventors: Eric H. Kuhrts, Woodside; David R. Friend, Menlo Park; Karen Yu, Sunnyvale; Jagdish Parasrampuria, San Mateo, all of Calif.

[73] Assignee: Venture Lending, Palo Alto, Calif.

[21] Appl. No.: 08/969,810

[22] Filed: Nov. 13, 1997

Related U.S. Application Data

[63] Continuation of application No. 08/564,974, Nov. 30, 1995, abandoned, which is a continuation-in-part of application No. 08/347,601, Dec. 1, 1994, abandoned, which is a continuation-in-part of application No. 08/206,421, Mar. 4, 1994, abandoned, and application No. 08/269,803, Jun. 30, 1994, abandoned, which is a continuation-in-part of application No. 08/078,891, Jun. 17, 1993, abandoned.

[51] Int. Cl.$^6$ .............. A61K 9/16; A61K 47/30; A61K 47/36
[52] U.S. Cl. ............. 424/500; 424/451; 424/452; 424/464; 424/465; 514/922; 514/951; 514/960; 514/974
[58] Field of Search .................. 424/456, 468, 424/496, 500, 464, 465, 451, 452; 514/951, 922, 960, 974

[56] References Cited

U.S. PATENT DOCUMENTS

| | | |
|---|---|---|
| 510,266 | 4/1893 | Acharya . |
| 3,065,143 | 11/1962 | Christenson et al. . |
| 4,126,672 | 11/1978 | Sheth et al. . |
| 4,140,755 | 2/1979 | Sheth et al. . |
| 4,167,558 | 9/1979 | Sheth et al. . |
| 4,242,355 | 12/1980 | Nedelec et al. . |
| 4,369,182 | 1/1983 | Ghyczy et al. . |
| 4,389,393 | 6/1983 | Schor et al. . |
| 4,540,566 | 9/1985 | Davis et al. . |
| 4,601,895 | 7/1986 | Streuff et al. . |
| 4,666,716 | 5/1987 | Sheth et al. . |
| 4,681,756 | 7/1987 | Mergens et al. . |
| 4,795,327 | 1/1989 | Gaylord et al. . |
| 4,844,905 | 7/1989 | Ichikawa et al. . |
| 4,849,229 | 7/1989 | Gaylord . |
| 4,867,979 | 9/1989 | Sheth et al. . |
| 4,994,276 | 2/1991 | Baichwal et al. . |
| 5,010,061 | 4/1991 | Speck et al. . |
| 5,047,248 | 9/1991 | Calanchi et al. . |
| 5,096,714 | 3/1992 | Kuhrts . |
| 5,096,717 | 3/1992 | Wirth et al. . |
| 5,108,921 | 4/1992 | Low et al. . |
| 5,118,510 | 6/1992 | Kuhrts . |
| 5,147,655 | 9/1992 | Ibsen . |
| 5,169,639 | 12/1992 | Baichwal et al. . |
| 5,174,998 | 12/1992 | Ijitsu et al. . |
| 5,211,957 | 5/1993 | Hagemann et al. ............ 424/466 |
| 5,260,304 | 11/1993 | Gergely et al. . |
| 5,288,500 | 2/1994 | Ibsen ............................ 424/489 |
| 5,292,518 | 3/1994 | Kuhrts . |
| 5,292,534 | 3/1994 | Valentine et al. . |
| 5,427,799 | 6/1995 | Valentine et al. . |
| 5,445,826 | 8/1995 | Kuhrts ............................ 424/451 |

FOREIGN PATENT DOCUMENTS

| | | |
|---|---|---|
| 0080673 | 6/1983 | European Pat. Off. . |
| WO 93/18755 | 9/1993 | WIPO . |

OTHER PUBLICATIONS

Corrente, (1954) "A Method for Appraisal of Antacid capacity," *Journal of the American Pharmaceutical Association* XLIII:242–245.

Hardt et al., (1954) "Improved Antacid Therapy of Peptic Ulcer," *American Journal of Digestive Diseases* 21:353–357.

Dale et al., (1955) "A Study of Antacids," *Journal of the American Pharmaceutical Association* XLIV:170–177.

Schlakman et al., (1957) "A Comparative Study of Commercially Available Guar Gums" *Drug Standards* 25:149–154.

Clarke et al., (1991) "Suppression of Thromboxane $A_2$ but not of Systemic Prostacyclin by Controlled–Release Aspirin," *The New England Journal of Medicine* 325:1137–1141.

Wilson et al., (1984) "Pharmacokinetic and In Vivo Scintigraphic Monitoring of a Sustained Release Acetylsalicylic Acid Formulation," *International Journal of Pharmaceutics* 18:1–8.

Harju, (1984) "Guar Gum Benefits Duodenal Ulcer Patients by Decreasing Gastric Acidity and Rate of Emptying of Gastric Contents 60 to 120 Minutes Postprandially," *The American Surgeon* 12:668–672.

Harju et al., (1985) "Effect of Gur Gum Added to the Diet of Patients with Duodenal Ulcer," *Journal of Patenteral and Enteral Nutrition* 9:496–500.

Park et al., (1984) "Biodhesiive Polymers as Platforms for Oral—Controlled Drug Delivery: Method Study Bioadhesion," *International Journal of Pharmaceutics* 19:107–127.

Rafatullah et al., (1994) "Gastric Anti—Ulcer and Cytoprotective Effects of Cyamosis tetragonoloba (Guar) in Rats" *J. Pharmacog.* 32(2):163–170.

Clarke, et al. (1991) Suppression of thromboxane A2 but not systemic prostacyclin by controlled—release aspirin. *New Eng. J Med*, 325 (16):1137–1141.

Isaksson, et al. (1982) In vitro inhibition of pancreatic enzyme activities by dietary fiber. *Digestion*, 24:54–59.

(List continued on next page.)

*Primary Examiner*—Robert H. Harrison
*Attorney, Agent, or Firm*—Cooley Godward LLP

[57] ABSTRACT

An oral-delivery pharmaceutical composition for reducing the gastric irritation effect of an NSAID in the upper GI tract of a mammal. The composition includes (a) a mucosal protective amount of a pharmaceutically-acceptable hydrocolloid gum obtainable from higher plants, (b) a dispersion-enhancing amount of another excipient and (c) a therapeutically-effective amount of an NSAID. Also disclosed is a process for preparing the composition and a method for reducing the gastric irritation effect of the NSAID by administering the composition. Also, disclosed is a composition particularly useful for preparing an aqueous suspension.

21 Claims, No Drawings

OTHER PUBLICATIONS

Barth and Smith (1981) High—performance size—exclusion chromatography of guar gum. *J. Chromatog*, 206:415–415.

Damge, et al. (1988) New approach for oral administration of insulin with polyalkylcyanoacrylate nanocapsules as drug carrier. Diabetes, 37:246–251.

Bhalla et al. Sustained Release Matrices for Quinidine Sulphate Tablets. Indian Drugs, Dec. 1987, vol. 25, No. 3, pp. 104–107.

Baveja et al. Examination of Natural Gums and Mucilages as Sustaining Materials in Tablet Dosage Forms. Indian Journal of Pharmaceutical Sciences, 3–4/1988, 50(2), pp. 89–92.

NSADI DELIVERY EMPLOYING A POWDERED HYDROCOLLOID GUM OBTAINABLE FROM HIGHER PLANTS

CROSS REFERENCES

This patent application is a continuation of U.S. application Ser. No. 08/564,974, filed Nov. 30, 1995, which is a continuation-in-part application of application U.S. Ser. No. 08/347,601 (filed Dec. 1, 1994), now abandoned, which in turn is a continuation-in-part of U.S. Ser. No. 08/206,421 (filed Mar. 4, 1994), now abandoned, and of application U.S. Ser. No. 08/269,803 (filed Jun. 30, 1994), now abandoned, which in turn is a continuation-in-part of U.S. Ser. No 08/078,891 (filed Jun. 17, 1993), now abandoned. All of the foregoing patent applications are incorporated herein by reference in their entirety.

TECHNICAL FIELD

This invention relates to mucosal protective pharmaceutical compositions comprising an NSAID, a hydrocolloid gum and other excipients. The invention also relates to a process for preparing such compositions and a method for treating certain conditions in humans by administering the compositions.

BACKGROUND

Non-steroidal anti-inflammatory drugs (NSAIDs) including aspirin have been used successfully in large numbers of patients with arthritis (including rheumatoid and osteoarthritis), and dysmenorrhea to relieve mild to moderate pain. It is well recognized that NSAIDs have a high incidence of gastrointestinal (GI) side effects. Serious GI adverse events such as bleeding, ulceration, and perforation can occur at any time in patients treated with regular doses of aspirin or other NSAIDs. The incidence of such adverse events ranges from 1–4% for studies without routine endoscopic surveillance to about 16% in studies where patients undergo regular endoscopic assessments.

The adverse GI effects of NSAIDs are a major concern in the use of these otherwise effective therapies. To date the efforts to produce a NSAID without these GI side effects have produced only marginal improvements. Misoprostol, a prostaglandin analogue, has been approved as a therapy to prevent NSAID-induced mucosal injury. Unfortunately, this compound has its own limitations to use. Consequently, mucosal protection remains an issue with aspirin and other NSAIDs.

Conventional formulations for reducing gastric distress usually involve either using pH buffering agents, coating the drug particles with various substances that are resistant to digestion and embedding them in a tablet matrix, or capsule formulation that is resistant to disintegration in the stomach. These latter formulations usually delay the release of the drug until it gets past the stomach and further down in the jejunum where it is then released. However, no approach so far has provided a readily acceptable rapid release composition that moderates the ulcerogenic action of NSAID in some portions of the population. It is therefore desirable to find a formulation of an NSAID that would provide rapid onset of action and a mucosal protective effect for the subject to whom it is administered, that is, it would reduce the gastric distress and/or ulcerogenic effect of an NSAID when delivered to a subject in need thereof.

Polysaccharide gums of hydrocolloids are a diverse class of substances that are hydrophilic and swell when in contact with water. When hydrated, they exhibit various degrees of viscosity. Polysaccharide hydrocolloids may contain galactose, galacturonic acid residues, mannose and sometimes xylose and arabinose. Structurally, they are similar to hemicellulose and when dissolved in water produce mucilage or gel. Some common polysaccharides used in the food and pharmaceutical industry are pectin, galactomannan gums, such as guar gum and locust bean gum, algal polysaccharides, such as agar and carrageenan, modified celluloses such as the cellulose ethers and esters and bacterial gums such as xanthan. The viscosity of these various substances will vary depending upon their molecular weight and structure.

Harju and Sajanti reported that oral administration of large quantities of guar gum provided protection against stress-induced ulceration in the rat (In vivo 5:397–400, 1991). In addition, Rafatullah et al. reported that an ethanol extract of guar (not guar itself) provided protection against several models of mucosal injury in the rat, including ethanol, stress, sodium chloride, indomethacin, and sodium hydroxide (*Int. Jugaslov. Pharmacy* 32:163–170, 1994).

A significant problem associated with high-viscosity water-soluble polymers is their ability to hydrate. Hydration is particularly difficult when these polymers are compressed into solid dosage forms. Most of the polymers used as excipients in pharmaceutical dosage forms are used at fairly low levels (e.g., 2 to 5 weight %) and principally as fillers or diluents. Of all the water-soluble polymers, guar gum probably possesses the highest molecular weight and exhibits the greatest viscosity when hydrated. Guar gum has been used at such low levels in a variety of products such as Quinidex® brand quinidine sulfate, Sine-Off® brand aspirin and acetaminophen, Bayer® brand aspirin, and Premarin® brand estrogen tablets. No mucosal protective effect has been reported at such low doses. The molecular weight of guar gum is reported as in the range of $1-2 \times 10^6$ daltons (*J. Chromatogr.* 1981; 206, 410 and *Carbohyd. Polymers*, 1984; 4,299). Other hydrocolloids which come within the above limitations include solid dosage forms that contain about 5% by weight of high-viscosity gel-forming polysaccharides and are subject to surface gelation and the inability to fully hydrate the dosage form. Tablets containing elevated levels of high-viscosity polysaccharides begin to gel and hydrate, but the hydration stops at a certain point. The core of the tablet remains dry and therefore not all the drug may be released. The dissolution tests of such tablets demonstrate that only 40% to 70% of the drug is actually released after eight hours and, in many cases, even after 24 hours a significant amount of the drug is not released. At the other end of the spectrum, tablets containing high amounts of high-viscosity polysaccharides, when formulated differently, can result in dose dumping or the immediate release of the drug, and therefore cannot be used for sustained release formulations, because they immediately disintegrate upon reaching the stomach or in a dissolution vessel.

Thus, there is substantial interest in developing novel oral formulations (particularly tablets or capsules) which allow for the release of an NSAID for rapid onset of action while providing a mucosal protective effect on the gastrointestinal tract, i.e., the ulcerogenic effect of the NSAID is reduced.

OBJECTS OF THE INVENTION

An object of this invention is to provide a pharmaceutical composition containing a NSAID that exhibits reduced gastric irritation when delivered to a subject orally, as compared to presently available NSAID compositions.

Another object of this invention is to provide a pharmaceutical composition containing a NSAID that releases the NSAID at essentially the same rate and level as commercially available NSAID compositions, i.e. the composition does not alter pharmacokinetic profile of the NSAID.

Another object of this invention is to provide a pharmaceutical composition containing a NSAID that disperses in the stomach and upper GI tract quickly to ensure release of the NSAID and at the same time provide mucosal protection.

Another object of this invention is to provide a pharmaceutical composition containing a NSAID that meets the above objectives and can be prepared as a tablet or capsule.

Another object of this invention is to provide a pharmaceutical composition containing a NSAID that meets the above objects and is readily prepared using inexpensive, commercially available materials combined in a unique manner.

Still another object of this invention is to provide a pharmaceutical composition containing a NSAID that is prepared without using components that increase the difficulty of handling and storing the compositions of this invention.

Still another object of this invention is to provide a method for reducing the gastric irritancy of NSAID-containing compositions by including a mucosal protective amount of a hydrocolloid obtainable from higher plants in the composition.

Other objects of this invention will be apparent to those of skill in the art upon reviewing the following specification and claims.

SUMMARY OF THE INVENTION

One aspect of this invention is a pharmaceutical composition suitable for oral delivery of a non-steroidal anti-inflammatory drug (NSAID) as a unit dosage form, which composition exhibits a mucosal protective effect and which comprises (a) a mucosal protective amount of a pharmaceutically-acceptable powdered hydrocolloid gum obtainable from higher plants;

(b) a dispersion-enhancing amount of another pharmaceutically-acceptable excipient; and (c) a therapeutically-effective amount of a NSAID.

Another aspect of this invention is a method for reducing the gastric irritation effect of an NSAID while orally administering that NSAID, which method comprises orally administering a unit dosage form composition comprising (a) a mucosal protective amount of a pharmaceutically-acceptable powdered hydrocolloid gum obtainable from higher plants;

(b) a dispersion-enhancing amount of another pharmaceutically-acceptable excipient; and (c) a therapeutically-effective amount of a drug.

Still another aspect of this invention is a process for preparing an orally-administrable unit dosage form of an NSAID that has reduced gastric irritation, which process comprises combining a therapeutically-effective amount of the NSAID with an amount of a pharmaceutically-acceptable hydrocolloid obtainable from higher plants that is sufficient to decrease the gastric irritation effect of the NSAID when the NSAID-containing composition is orally administered.

Other aspects of this invention will be apparent to one of skill in the art from further reading this specification.

DESCRIPTION OF SPECIFIC EMBODIMENTS

In accordance with the subject invention, mucosal protective formulations are provided where the formulation comprises a solid dose of (a) a NSAID in a physiologically desirable amount, (b) a high viscosity, substantially linear, polysaccharide hydrocolloid (generally consisting of long mannan molecules with some side chain attachment as exemplified by guar gum and locust bean gum or other polysaccharides such as gum tragacanth or karaya gum) by itself or in conjunction with (c) another dispersion-enhancing excipient, where both the NSAID and the high viscosity hydrocolloid may be coated with lower viscosity hydrocolloids, particularly cellulosic.

Another broad aspect of this invention is a NSAID pharmaceutical composition that exhibits mucosal protective characteristics in a vertebrate animal to which it is orally administered and that comprises (a) a therapeutically effective amount of an NSAID absorbable through the upper gastrointestinal tract, (b) an amount of a powdered hydrocolloid gum obtainable from higher plants that results in a mucosal protective effect in the gastrointestinal system with drug transport to the subject's blood stream, and (c) other pharmaceutically-acceptable excipients that enhance the dispersion of drug and hydrocolloid in the stomach to provide the desired mucosal protective effect.

Another aspect of this invention is a solid dosage form NSAID pharmaceutical composition for administration to a human subject comprising , (a) 15% to 90% (w/w) of a powdered hydrocolloidal gum obtainable from higher plants (generally having a viscosity when fully hydrated of at least 75 cps for a 1% neutral aqueous solution at 25° C.), (b) 10% to 75% (w/w) of another pharmaceutically acceptable, dispersion-enhancing excipient, and (c) a therapeutically-effective amount of an NSAID that is absorbable through the upper gastrointestinal tract.

Alternatively, this invention can be viewed as an improvement in a composition comprising a therapeutically effective amount of an NSAID suitable for oral administration to a human subject in need thereof in combination with a suitable pharmaceutical excipient. The improvement comprises the combination of the NSAID with a powdered hydrocolloid gum obtainable from higher plants in an amount sufficient to provide a cytoprotective effect, i.e., to reduce the ulcerogenic effect of the NSAID.

The hydrocolloids used in the subject invention have high viscosity exhibited upon hydration, are normally linear (at least about 50% by weight or more of the compound is the backbone chain), and will normally have a high molecular weight, usually at least about $5 \times 10^5$ daltons, more usually greater than about $1 \times 10^6$ daltons. Generally, the hydrocolloid is a powdered hydrocolloid gum that is obtainable from higher plants and that exhibits a viscosity at 1% concentration in a neutral aqueous solution of at least about 75 centipoise per second (cps) at 25° C. after 24 h, using a Brookfield Viscometer (model LVF) with a #3 spindle at 90 rpm, preferably at least about $1 \times 10^3$ centipoise (cps), and most preferably at least about $2 \times 10^3$ cps. See Meer Corp., *An Introduction to Plant Hydrocolloids*. By "higher plant" is meant an organism of the vegetable kingdom that lacks the power of locomotion, has cellulose cell walls, grows by synthesis of or inorganic substances and includes the vascular plants (or Tracheophytes) of the division Spermatophyta, particularly those of the class Angiospermae. The gums may be extracted from the roots, legumes, pods, berries, bark, etc. Thus, higher plants do not include algae, flagellates, bacteria, slime molds, fungi, mosses, ferns, horsetails, and the like. Representative hydrocolloid gums obtainable from higher plants include guar gum, gum tragacanth, karaya gum (also referred to as karaya gum) and locust bean gum. Hydrocolloid gums most useful are those where the hydrocolloid is a polysaccharide hydrocolloid which is chemically designated as a galactomannan. Galactomannans are polysaccharides consisting of long chains of (1→4)-β-D-mannopyranosyl units to which single unit side chains of α-D-galactopyranosyl are joined by (1→6) linkages. Galactomannans are found in a variety of plants but differ in molecular size and the number of D-galactosyl side chains. The galactomannans useful in this invention are commonly found in the endosperms of the leguminosae. Examples of the family of legumes are set forth in Table 1 which shows the family and the percent endosperm content of leguminous seeds.

TABLE 1

Estimated Endosperm Content of Leguminous Seeds

| Family | Endosperm % | Family | Endosperm % |
|---|---|---|---|
| Acacia | 1–15 | Glottidium | 2 |
| Astragalos | 2–3 | Glymnocladus | 15 |
| Baryxylum | 30 | Indigofera | 20 |
| Caesalpinia | 8–40 | Lespedeza | 1–4 |
| Cassia | 10–60 | Leucaena | 15 |
| Cercidium | 20 | Lotus | 2–4 |
| Ceratonia (carob) | 50 | Lysiloma | 4 |
| Chamaecrista | 8–15 | Melilotus | 8–12 |
| Colvillea | 30 | Mimosa | 3–30 |
| Crotalaria | 8–25 | Onomois | 25 |
| Cyamopsis (guar) | 50 | Parkinsonia | 25 |
| Cytisus | 15 | Parryella | 20 |
| Dalea | 20 | Prosopis | 15 |
| Daubentonia | 10–15 | Schrankia | 12 |
| Delonix | 25 | Sesbania | 20 |
| Desmanthus | 15 | Sophora | 20–25 |
| Desmodium | 2 | Trifolium | 3–10 |
| Gleditsia | 30 | Virgilia | 20 |

Table 2 shows the approximate composition of some galactomannans from legume seeds and the percentage of anhydromannose residues versus the anhydrogalactose residues. As can be seen from Table 2, the percentage of anhydromannose may vary from about 50% to about 90% (e.g. 86%) of the composition of the galactomannan with the percent anhydrogalactose varying from about 10% (e.g. 14%) to about 50%.

TABLE 2

Approximate Composition of Some Galactomannans from Legume Seeds

| Name of Seed | Ahnydro-mannose % | Anhydro-galactose % |
|---|---|---|
| Caesalpinia spinosa (tara) | 71 | 26 |
| Caesalpinia cacalaco (huizache) | 69 | 28 |
| Ceratonia siliqua (carob, locust bean) | 80–86 | 20–14 |
| Cercidium torregyanurn (palo verde) | 73 | 22 |
| Delonix regia (flame tree) | 79 | 19 |
| Cyamopsis tetragonolobus (guar) | 64 | 36 |
| Gleditsia triacanthos (honey locust) | 71 | 26 |
| Gymnocladus dioica (Kentucky coffee) | 71 | 26 |
| Sophora japonica | 81 | 16 |
| Desmanthus illinoensis (prairie-mimosa) | 70 | 26 |
| Indigofera hirsuta (indigo) | 72 | 23 |
| Cassia leptocarpa (senna) | 65 | 21 |
| Crotalaria intermedia (rattlebox) | 64 | 28 |
| Crotalaria juncea (rattlebox) | 60 | — |
| Crotalia striata (rattlebox) | 60 | — |
| Trigonella foenurn graecum (fenugreek) | 52 | 48 |
| Medicago sativa (alfalfa) | 66 | 33 |

Preferably, the galactomannan that is most useful in this invention is derived from the cyamopsis tetragonolobus, commonly referred to as guar. This exhibits a percentage mannose residue of about 64% with a percent galactose residue of about 36%. Commercially available guar gum is about 66–82% galactomannan polysaccharide with protein, fat-extractable material, ash, moisture and other impurities making up the remainder of the composition: In general guar is available commercially in purities that meet NF requirements, namely it may contain up to 15% w water, 10% w protein, up to 7% w acid insoluble material and up to about 1.5% ash. Sources of commercially available guar gum are Aqualon Company, Wilmington, Del.; Meer Corporation, Cincinnati, Ohio; Stein Hall & Company; and TIC Gums, Inc. Others may be readily apparent to one of skill in the art. See for example "The Chemistry of Plant Gums and Mucilages" by Smith and Montgomery from the A.C.S. Monograph series, #141, 1959, Reinhold Publishing Co.

The amount of the hydrocolloid in the composition will be an amount that provides a mucosal protective effect as compared to a formulation of the drug which gives a standard release profile. Mucosal protection is also sometimes referred to as cytoprotection if the mechanism by which a composition works to protect the mucosal layer is at the cell level. For purposes of this application the term mucosal protective will be used as the mechanism of action is not known for certain to be at the cellular level where the protection is occurring. Mucosal protective more accurately reflects the protection of mucous layer of the stomach, i.e. gastric irritation is reduced. Gastric irritation includes such adverse gastrointestinal (GI) side effects such as bleeding, ulceration and perforation of the mucosal lining of the stomach and upper GI tract. Mucosal protection is the ability of a composition to defend against or prevent gastric mucosal lesions or damage that might occur as a result of NSAID administration. In general, the amount of the hydrocolloid obtainable from higher plants that provides mucosal protection will be from about 15% by weight to about 90% by weight, based on the total pharmaceutical composition. Preferably, the amount of the hydrocolloid will be between about 20% by weight to about 75% by weight, and more preferably about 40% by weight to about 60% by weight. As mentioned previously, guar gum is a particularly preferred hydrocolloid which is particularly useful in the various aspects of this invention.

In general, the particle size of the hydrocolloid, particularly guar gum, used in the composition will have a median diameter size of more than about 125 microns ($\mu$), i.e., about 50% of the particle mass in the composition be below 125$\mu$ in diameter and about 50% of the particle mass will be above about 125$\mu$ diameter. Preferably, the median particle size of the hydrocolloid will be more than about 150$\mu$ with a distribution of about 75 to about 300$\mu$. More preferably, the particles will be greater than 150$\mu$ up to 300$\mu$, i.e. about 90% of the particle mass will have a particle size of 125$\mu$ or more, up to about 300$\mu$. Sources of guar gum are readily available commercially, but the brand referred to as SUPERCOL® G3, having a particle size of about 75 to about 300 microns is found to be particularly useful. The SUPERCOL guar gum is available from the Aqualon Company, Wilmington, Del. Other sources include Henkel, a division of Emery Group, Cincinnati, Ohio or the Meer Corporation. The desired particle sizes can be obtained by milling larger particles of guar gum and sifting to get particles to the desired size, or sifting to obtain larger particle sizes. The size distribution of the particles may be determined by standard sieve separation methods, i.e., by passing the guar particles though sieves having known mesh sizes (and known apertures) and collecting the retained or non-retained fractions. The same methods are useful for obtaining guar particles of desired sizes for use in preparing the composition of the invention.

By varying the particle size distribution of the hydrocolloid (e.g. guar gum) within the range, the release characteristics of the composition of this invention may be varied. Generally, the smaller the particle size, the slower the NSAID is dispersed. Conversely, the larger (or coarser) the particle size, the more quickly is the NSAID dispersed. By using a mixture of particle sizes and adjusting in accordance with the NSAID used, compositions are obtained with particularly useful delivery characteristics. The type and amount of other excipients will also effect the characteristics of the compositions of this invention.

Generally, the pharmaceutical composition of this invention is a particle mass of a solid dosage form that is administered orally. Thus, the composition is neither a liquid nor a gas, but a solid which may be a powder for suspension in water, a tablet or a capsule, preferably the latter two. In general, the total amount in the solid dosage form will be that amount referred to as a unit dosage. Generally, for a capsule or tablet this will be an amount that can be swallowed by a human subject and may vary from a total of about 100 milligrams to about 1500 mg, preferably no more than about 1200 mg and particularly no more than 1000 mg. In general the tablet or capsule will be at least about 350 mg for enough of the hydrocolloid to be present to provide a mucosal protective effect. Generally in a unit dosage it is preferred to have about 240 milligrams of the hydrocolloid such as guar gum but generally less than about a gram. For children, the size of the tablet or capsule may be significantly less than for adults, and for elderly patients who have difficulty swallowing, the total amount may be less than what would be viewed as a normal amount for adults. The total amount of material in a unit dosage depends in part on the activity of the drug used in the composition. A particularly useful composition for patients who have difficulty swallowing pills is one that is a unit dosage suitable for suspension in about an 8 ounce glass of water. This unit dosage amount is generally less than about 5 grams, preferably less than about 2.5 grams.

The therapeutically-effective amount of the NSAID in the unit dosage form will be that amount of material which is calculated to give the desired therapeutic effect upon oral administration of the material. If the NSAID is highly active (or is like aspirin for low dosage treatment to prevent stroke or thromboses) and very little of the material is needed, then the total size of the unit dosage form will be less than if the drug requires a larger amount to get the desired physiological effect. Thus, the amount of NSAID in the composition depends on the activity of the NSAID and this amount may vary from about 0.1% weight to about 75% weight, generally in a tablet or capsule unit dosage form no more than about 45% weight, preferably about 5% to about 45% by weight (generally no more than 35% weight) and more preferably from about 10% weight to about 25% weight. For a non-tablet or non-capsule unit dosage form, e.g., a powder for suspension in water the percent weight active will be about 10% to about 75% by weight, preferably about 15% to about 50% by weight.

A wide variety of NSAIDs may be employed, but the subject formulations find particular physiological advantage with aspirin. Individual NSAIDs suitable for use in compositions described in such publications as Goodman & Gilman's *Pharmaceutical Basis for Therapeutics*, (Goodman and Gilman) 8th edition (1990), Chap. 26; *The Physician's Desk Reference* (1994-PDR); and Berger's Medicinal Chemistry. As such, these publications are incorporated herein by reference. Representative NSAIDs and families of NSAIDs useful in the compositions of this invention include the salicylates, pyrazolons, indomethacin, sulindac, the fenamates, tolmetin, propionic acid derivatives, and the like. Specific compounds include salicylic acid, aspirin, methyl salicylate, diflunisal, salsalate, phenylbutazone, indomethacin, oxyphenbutazone, apazone, mefenamic acid, meclofenamate sodium, ibuprofen, naproxen, naproxen sodium, fenoprofen, ketoprofen, flurbiprofen, piroxicam, diclofenac, etodolac, ketorolac, aceclofenac, nabumetone, and the like. Aspirin is preferred.

In general, the weight ratio of the NSAID to the hydrocolloid is a ratio of about 1:0.6 to 1:500. Preferably, the weight ratio of the drug to said hydrocolloid of from about 1:1 to 1:15 and more preferably from about 1:1 to 1:3.

In general it is preferred to design a composition that does not alter the pharmacokinetic profiles (i.e. the rate and extent of absorption) of the NSAIDs (e.g. aspirin) significantly in comparison to less or non-mucosally-protective commercially-available products. Thus, the composition will be designed to either disperse rapidly or swell to release the NSAID quickly. The exact characteristics of the composition may be adjusted by the inclusion of the other dispersion-enhancing excipients. Other such excipients are included in the composition of this invention to help improve dispersion, i.e., disintegration of the composition to avoid the concentration of a NSAID in one place. This may be achieved by including a highly soluble component that allows water to penetrate, e.g. by channeling or a swellable component that forces the composition to expand and disintegrate. Generally the dispersion will take place under standard test conditions, as discussed in Example 3, in less than about 5 minutes. As used herein, the term "excipient" may include all excipients present in the dosage form, including all components other than the drug entity and the hydrocolloid gum from higher plants. A plurality of excipient substances may be present in any dosage form, and may include multiple substances having similar pharmaceutical function (e.g., lubricants, flavorants, disintegrants, binders, diluents) or similar structure (e.g., a mixture of monosaccharides). Such excipients are present in an amount sufficient to provide the composition with the desired characteristics, i.e. to enhance dispersion of the drug and hydrocolloid, and will generally be present at a level of about 5% by weight to about 75% by weight, preferably about 10% by weight to about 50% by weight and more preferably about 10–25% by weight. For a dosage suitable for suspension no more than about 5% to 10% by weight is needed. Excipients may be selected from many categories known in the pharmaceutical arts, but generally will be hydrophilic entities that absorb water readily and dissolve or that expand upon contact with water to aid in dispersion. Examples of the former include carbohydrates such as mono- and disaccharides (i.e., lactose, sucrose, glucose, fructose, galactose); oligosaccharides such as dextrin; hydrocolloid polysaccharides such as cellulose, microcrystalline cellulose, semisynthetic cellulose ethers and derivatives thereof such as, carboxymethylcellulose (CMC), carboxypolymethylenecellulose (CPMC), hydroxypropylcellulose (HPC), hydroxypropylmethylcellulose (HPMC), sodium CMC, and methylcellulose (MC); polyvinylpyrolidone (PVP), crospovidone (a crosslinked PVP), sodium starch glycolate, and colloidal silicon dioxide, represented by Syloid® brand colloidal silicon dioxide. In general, the hydrocolloid obtainable from higher plants will be the largest weight component of the composition, although in some instances, one or more other components may be present in greater weight percent. Representative disintegrants that are found to be particularly useful to enhance dispersion of the NSAID include the following, which may be used alone or in combination with each other: Avicel® brand microcrystalline cellulose, Crospovidone® brand PVP, lactose, Explotab® brand sodium starch glycolate (in small quantities and generally combined with another excipient), Syloid® brand colloidal silicon dioxide, and the like.

The combination of excipients, such as other hydrocolloids, can be used to adjust the rate of hydration of the solid dosage formula, as well as allowing for a lower level of the powdered hydrocolloid gum obtainable from higher plants to be used, therefore, resulting in some cases in a less bulky tablet. In addition, combinations of hydrocolloids may provide for greater degrees of control over drug delivery, but care must be taken in preparing the combinations, since depending upon the other excipients, there may be adverse effects. The adverse effects may include incomplete hydration, drug-dumping, and the like. The amount and choice of the excipients will also be affected by the other ingredients present in the formulation, so that one may modulate the effects of the other hydrocolloids by the other components.

Another category of carbohydrates useful as another dispersion-enhancing excipient is the "lower organism" hydrocolloidal gums from bacterial, fungal, or algal sources, such as agar, xanthan, and carrageenan. These may be used in conjunction with the highly viscous hydrocolloidal gums from higher plants, such as guar, as described herein. When such lower organism gums are included, they generally will be present in amounts no greater than the amount of gum from higher plants, on a weight basis, and usually no greater than 75%, often 50%, less than 10–25%, of the amount of hydrocolloid gum from higher plants.

Another excipient that may be present in the composition is in the category known in pharmaceutical arts as a binder. Generally a binder tends to bind or aggregate particles, and are often employed in tabletting to reduce friability and impart hardness to the composition. Thus careful consideration must be given to the amount of binder present so that the dispersion-enhancing aspect of the composition is not significantly reduced while at the same time improving hardness. Generally the hardness rating of a tablet will be sufficient for the tablet to be stored, handled, packaged and shipped without damaging a significant percentage of tablets in the overall processing steps. Usually the minimum hardness rating is about 6 kP and preferably is about 8 kP or more. The designation "kP" is the force required to crush a tablet, generally expressed in Kilograms. Binders are described in numerous sources, e.g., *Remington's Pharmaceutical Sciences*. Strong binders in general will be employed in small proportions, usually less than about 10% wt, often less than about 5% wt, frequently less than about 2% wt, and occasionally less than 0.5% of the weight of the dosage form. An exemplary group of strong binders are carboxypolymethylene, referred to as CARBOPOL and CARBOMER. In large amounts, they interfere with disintegration of the dosage forms, and should be used in small proportions or avoided altogether.

Non-gas-forming filler materials or diluents are typically inert substances for dispersing the compound within the particle mass while being conducive to hydration of the mass during migration through the stomach. Such a diluent may simply serve to dilute the drug and aid in processing and/or dispersion of the NSAID. Mineral salts that dissolve in gastric juice may be used, thereby aiding in the disintegration of the dosage form and hydration of the hydrocolloids. Previously, salts which form gas in the gut, such as carbonates and bicarbonates, had been shown to be needed in dosage forms with guar gum. The present invention may employ non-gas-forming mineral salts such as alkaline earth (e.g., $Ca^{+2}$, $Mg^{+2}$) phosphates and sulfates, but preferably the composition of this invention is free of any gas-forming mineral salts because they generally absorb water readily and make the compositions more difficult to handle and store.

Other excipients may be included to impart lubricating properties to the composition to aid in release from tabletting press or to assist in making the composition flow better. Such components include fatty acids or their salts (e.g., stearic acid or magnesium stearate) and waxes. Other excipients may include synthetic emulsifiers (e.g., sodium lauryl sulfate) and surfactants, such as polyakylene glycols (e.g., polyethylene glycol-PEG). In certain embodiments, the amount of polyethylene glycol may be restricted to be present in less than 20% relative to the weight of the drug, particularly with PEGs of mean molecular weight greater than 2,000 Daltons.

The following Table 3 sets forth representative compositions of this invention that are useful for tablet and capsule formulations. The table shows the approximate relative weight percent of each component that may be used. It is to be understood that the total amount in the composition is a unit dosage that may vary between about 100 mg and about 1500 mg, but generally will be less than 1200 mg and preferably less than about 1000 mg. The "hydrocolloid" in the first column refers to a hydrocolloid gum obtainable from higher plants in accordance with this invention. This may be a gum having a preferred particle size as discussed herein, preferably between about $150\mu$ to about $300\mu$. The excipient may be a single excipient or a mixture of excipients as discussed hereinbefore. The numbers are simply meant to be approximation of the proportions of components used.

TABLE 3

| Hydrocolloid | NSAID | Other Excipient |
| --- | --- | --- |
| 75 | 5 | 20 |
| 75 | 10 | 15 |
| 75 | 20 | 5 |
| 70 | 20 | 10 |
| 65 | 20 | 15 |
| 60 | 35 | 5 |
| 55 | 30 | 15 |
| 55 | 15 | 30 |
| 50 | 30 | 20 |
| 50 | 40 | 10 |
| 50 | 15 | 35 |
| 45 | 40 | 15 |
| 40 | 35 | 25 |
| 40 | 40 | 20 |
| 35 | 30 | 35 |
| 30 | 50 | 20 |

The particle mass is blended by standard methods, i.e., by combining the specified components and mixing them in a granulator or other type of blender.

The following Table 4 sets forth a summary of the Broad, Preferred and More Preferred % weight ranges for the components of the compositions of this invention for tablet and capsule formulations.

TABLE 4

|  | Broad | Preferred | More Preferred |
| --- | --- | --- | --- |
| Hydrocolloid | 15–90 | 20–75 | 40–60 |
| NSAID | 0.1–75 | 5–45 | 10–35 |
| Other Excipients | 5–75 | 10–50 | 10–25 |

For providing a mucosal protective effect, the particle mass described in hereinbefore may be bound together by encapsulation or compacted as a tablet, optionally coated with a non-enteric coating material. The tablet or capsule is prepared so as to (i) prevent dispersal of the particle mass until the particle mass has reached the stomach, (ii) to dissolve in the stomach in a manner that allows a hydrated gel layer to form around the entire particle mass, forming a guar-compound bolus, and (iii) to dissolve relatively quickly after the hydrated gel layer has formed to allow compound release from the bolus.

In one embodiment, the holding means is a capsule, such as a gelatin capsule available from Elanco Qualicaps (Indianapolis, Ind.) or Capsugel (Warner Lambert, Morris Plains, N.J.). Other suitable capsules include soft elastic capsules.

Prior to encapsulation or coating, the particle mass can be gently compressed in a dry granulation process to facilitate manufacture or to modify dissolution properties of the mass. This process leads to formation of tablet triturates.

If the particle mass is held together in the form of a tablet, the composition of the particle mass is generally the same as for the encapsulated forms described above. The tablet is formed by conventional means, at a compression pressure of about 3,000 to about 5,000 psi. Generally, the tablet should be sufficiently cohesive to allow formation, in the stomach, of a hydrated gel layer which coats the surface of the tablet and keeps the tablet together as a single bolus until the tablet becomes fully hydrated and fully dispersed.

Optionally, the tabletted particle mass can be coated with a coating, e.g., lactose or cellulose derivatives that improve the ease of swallowing, prevent swelling and improve the pharmaceutical appearance. Such coatings can be simple sugars such as lactose, sucrose and the like or may be high viscosity hydrocolloid or other, particularly lower viscosity, hydrocolloids, particularly ionic hydrocolloids, more particularly cellulosic derivatives, such as ethyl cellulose. On the other hand a hydrocolloid may be used by itself or in conjunction with a neutral cellulosic hydrocolloid. The coating may be achieved in a fluid bed granulator prior to packaging.

The composition of this invention, particularly as it applies to aspirin or ketoprofen, is particularly effective as a powder in a unit dosage form that is suitable for adding to water to form a suspension. Generally the hydrocolloid will be of lesser viscosity so that the aqueous suspension is not too thick. Thus, a hydrocolloid such as guar gum having coarser particles and lower viscosity is preferred as the hydrocolloid. An example is SUPERCOL G3 guar gum (particle size distribution of about 75 microns to about 300 microns with a median particle size above about $150\mu$). The unit dosage amount as a powder suitable for suspension will be about 800 mg to about 5 grams, generally less than about 4 grams, and preferably less than 2.5 grams. Generally the NSAID, e.g., aspirin, will be present in an amount from about 10% to about 75% by weight, preferably about 15% to about 50% by weight; with hydrocolloid being present in an amount from about 20% to about 90% by weight, preferably about 50% to 85% by weight; and the other excipient (e.g., flavoring, flavor aids, sugar, etc.) present in an amount less than 5% by weight.

Process for Making

Another aspect of this invention is a process for preparing a composition of this invention. In general, a composition according to this invention is prepared by thoroughly mixing the components of the composition of this invention and preparing a unit dosage form that is suitable for oral administration and that exhibits a mucosal protective effect to a subject to whom it is administered. The components are mixed as dry, particulate material in the preparations and having the particle size distribution set out hereinbefore to give a composition with the components uniformly distributed throughout the composition. Generally the mixing is achieved using standard mixing technology known in the art such as that set forth in *Remington's* (Eighteenth Edition) at pp. 1627–1629. Representative equipment includes rotating-shell mixers (e.g. a cross-flow blender), fixed shell mixers, Muller mixers, vertical impeller mixers, motionless mixers and the like. The resulting mixture is then prepared as a unit dosage, e.g., as a tablet or, preferably, as a capsule in accordance with known techniques such as those set forth in *Remington's* (Eighteenth Edition) in Chapter 89, which is incorporated herein by reference.

Alternatively a dry granulation process can be used to prepare compositions of this invention. In this process the components of the NSAID and the hydrocolloid (of the desired particle size) are thoroughly mixed with the dispersion-enhancing excipient as discussed herein before. The resulting blend is compressed to form large caplets having an average hardness rating of about 8–12 Kp, preferably about 10 Kp. These caplets are then crushed and sieved using an 18 and 40 mesh screen, and the particles that are retained on the 40 mesh screen (e.g., particles of $425\mu$ size but generally between about $400$–$500\mu$) are then combined with a lubricant and tabletted.

Another aspect of this invention may be viewed as an improvement. In a process of preparing an orally administrable dosage form of an NSAID suitable for human administration that comprises combining a therapeutically effective amount of the NSAID with suitable pharmaceutical excipients, the improvement that comprises combining the NSAID with a powdered hydrocolloid gum obtainable from higher plants in an amount sufficient to reduce the ulcerogenic effect of the NSAID.

Method of Administration

Still another aspect of this invention is a method of orally administering an NSAID to a mammalian subject (preferably human) in need thereof wherein the drug is orally delivered in a unit dosage as a composition of this invention. Another way of viewing the method this invention is as an improvement. In a method for orally administering a therapeutically effective amount of an NSAID to a human subject in need thereof, the improvement comprising orally administering the NSAID in combination with a powdered hydrocolloid gum obtainable from higher plants in an amount sufficient to provide a mucosal protective effect for the subject. Generally, that amount sufficient to provide such a mucosal protective effect is set forth hereinbefore in the discussion of the composition of this invention. The dosages for NSAIDs may be readily found in the "Physician's Desk Reference" or in "Goodman and Gilman," and as such they are incorporated herein by reference.

While the invention has been described with reference to specific embodiments, it will be appreciated that various modifications and changes may be made without departing from the spirit and scope of the invention. The following representative examples are set forth to provide further guidance in how to make and use the invention, but are not intended to limit the scope of the invention in any way.

EXAMPLE 1

This example shows the mucosal protective effect of a hydrocolloid gum obtainable from higher plants (guar gum) in an NSAID (aspirin) formulation administered to rats.

Tests were conducted in the aspirin-induced gastric ulcer model. Rats were dosed as indicated below. Five hours after dosing, rats were sacrificed and stomachs were examined for the presence of gastric lesions. A total of 6 treatments were tested. Each treatment was tested in 12 rats.

1. Aspirin alone—control
2. Aspirin with 0.1% guar gum
3. Aspirin with 1.0% guar gum
4. Aspirin with 5.0% guar gum
5. Guar gum 5.0% alone
6. No treatment The treatments were prepared immediately prior to use. The aspirin treatments were prepared by suspending 2.00 grams of fine mesh aspirin in 100 ml water (plus 0.1% Tween 80) and then adding the specified amount (i.e. 0, 0.10, 1.00, or 5.00 grams) of Guar gum. The Guar gum 5.0% alone treatment was prepared as above except the aspirin was omitted. All dosing preparations were warmed to about 100° C.; uniformity of suspensions was ensured by constant stirring.

Sprague-Dawley male rats, 148 to 190 grams, were individually-housed under standard Vivarium conditions. After arrival, rats were allowed to acclimate in house for a minimum of 5 days before initiation of testing. Rats were fasted (water ad libitum) for 18 hours prior to testing. Treatments 1–6, assigned to rats in random fashion, were administered orally (gavage) at the rate of 10 ml/kilogram (kg).

Five hours after treatment, each rat was sacrificed by carbon dioxide inhalation. The abdomen was opened. The stomach was removed, opened along the greater curvature, examined for the presence of lesions, and assigned a severity grade according to the following scale:

0 No lesions
1 <5 lesions, at least 1 lesion<2 mm
2 <5 lesions, at least 1 lesion>2 mm
3 5 to 10 lesions, all<2 mm
4 5 to 10 lesions, at least 1 lesion>2 mm
5 >10 lesions, all<2 mm
6 >10 lesions, at least 1 lesion>2 mm In order to eliminate bias and reduce subjective variation, all ulcer grading in the study was performed in single-blind fashion by the same well-experienced grader. For each stomach, the severity score was recorded.

Data are expressed using the absolute values. For each treatment group, results are presented as means±standard errors of the means (s.e.m.). Statistical significance of differences between means were determined by analysis of variance followed by Neumann-Kuels multiple comparisons test.

Results, presented as means±s.e.m., are summarized in Table 3. The results show that guar gum protects against aspirin-induced gastric lesions. In control rats, mean ulcer severity was 5.8. In rats receiving guar gum 0.1%, 1.0%, and 5.0%, respectively, mean severities were 4.0, 3.6, and 2.7. Thus compared to control, reductions in ulcer severity were 30, 38, and 54 percent, respectively. All differences were statistically significant (p<0.05).

TABLE 5

| Treatment | Ulcer Grade |
|---|---|
| Aspirin Alone (control | |
| mean | 5.8 |
| ± | 0.2 |
| Aspirin plus Guar Gum 0.1% | |
| mean | 4.0* |
| ±sem | 0.5 |
| reduction (%) | 30.4 |
| Aspirin plus Guar Gum 1.0% | |
| mean | 3.6* |
| ±sem | 0.7 |
| reduction (%) | 37.7 |
| Aspirin plus Guar Gum 5.0% | |
| mean | 2.7* |
| ±sem | 0.5 |
| reduction (%) | 53.6 |
| Guar Gum 5.0% Alone (control) | |
| mean | 0.2* |
| ±sem | 0.1 |
| reduction (%) | 97.0 |
| No Treatment (control) | |
| mean | 0.1* |
| ±sem | 0.1 |
| reduction (%) | 98.6 |

*significantly different from aspirin alone, p < 05

In the aspirin control group, the mean (±s.e.m.) ulcer severity was 5.75±0.18; stomachs from 11 of the 12 rats had ulcer severity scores of 5 or greater.

In rats receiving aspirin with guar gum 0.1%, 1.0%, and 5.0%, mean severities were 4.00±0.51, 3.58±0.71, and 2.67±0.50, respectively; compared to control, these values represent reductions in ulcer severity of 30, 38, and 54 percent. All differences were statistically significant (p <0.05). In rats receiving aspirin with guar gum 0.1%, 1.0%, and 5.0%, stomachs from 4 of 12, 5 of 12, or 1 of 12, respectively, had ulcer severity scores of 5 or greater.

In rats receiving guar gum 5.0% alone, the gastric mucosa of all rats appeared to be in perfect condition. Stomachs of 2 of the 12 rats each exhibited one very small imperfection (lesion severity grade 1), thus the mean severity for the group was 0.17±0.11 (of course, p<0.05 cf. aspirin control).

In rats receiving no treatment the gastric mucosa of all rats appeared to be in perfect condition. The stomach of 1 of the 12 rats exhibited one very small imperfection (lesion severity grade 1), thus the mean severity for the group was 0.08±0.08 (of course, p<0.05 cf. aspirin control).

EXAMPLE 2

This example shows the mucosal protective effect (i.e. the reduction of gastrointestinal irritancy) of a hydrocolloid gum obtainable from higher plants (guar gum) in NSAID (aspirin) formulation administered to humans.

This was a single-blind, parallel-group, multiple-dose study conducted on a total of 44 healthy subjects who were randomly assigned to treatment with either aspirin alone or one of three aspirin/guar combinations. Eleven subjects were assigned to one of each of the following treatment groups:

Treatment A: Aspirin 650 mg (Tablet)

Treatment B: Aspirin 650 mg/0.1 wt % guar gum (Powder)

Treatment C: Aspirin 650 mg/0.6 wt % guar gum (Powder)

Treatment D: Aspirin 650 mg/1.4 wt % guar gum (Powder)

Each subject received a total of 12 oral doses in an 8 ounce glass of water with the test medication over a 72-hour period. Assessments were primarily based on endoscopic evaluations of gastroduodenal irritancy performed 4 hours after the first dose of test medication, and 3 hours after the final administration of the test medication on the fourth study day. To ensure that all study subjects had normal gastroduodenal mucosa at baseline, an endoscopic evaluation was also performed before subjects were randomized. Healthy volunteers ranging from 18 to 45 years (mean age, 30 years) receives the treatment. Doses of test medication were administered on a QID regimen on an empty stomach at least 1 hour before any meal.

Endoscopy was used to assess the extent and severity of gastric and duodenal damage. During an endoscopic examination of the stomach and duodenum, the number and location of submucosal hemorrhages, erosions, and ulcerations were determined by the endoscopist, who was unaware of the formulation administered to the subjects. Based on these findings, the menorrhagic damage was graded on a 0–4 scale and the erosive damage was graded on a separate 0–4 scale. The stomach and duodenum were graded separately. Endoscopy was performed 4 hours after the first does on Day 1 to assess acute irritancy and on Day 4 to assess overall, or "pharmacological" steady-state, irritancy.

Plasma concentrations of acetylsalicylic acid and salicylic acid were used to assess absorption of the aspirin from the test formulations.

The Kruskal-Wallis test was used to compare the distribution of scores across treatments. Wilcoxon's Rank Sum test was used for pairwise comparisons between each of the aspirin/guar formulations vs. aspirin alone. When grouping the scores to determine the presence vs. absence of irritancy and sever vs. nonsevere damage, the Mantel-Haenszel test was used to test for a decrease in irritation with increasing guar dose. Fisher's Exact test was also used to determine pairwise differences between the aspirin/1.4% guar dose vs. aspirin alone.

To determine whether guar gum affected the absorption of the aspirin, blood samples were obtained at various times following the first dose of study mediation. In this pharmacokinetic sampling paradigm, the pharmacokinetic profiles of acetylsalicylic acid were similar among treatment formulations, as were profiles of salicylic acid.

Endoscopic evaluation of the mucosal damage caused by NSAIDs, including aspirin, in normal volunteers has been shown to be predictive of the gastrointestinal effects of these compounds in patient populations. Endoscopy results based on the analysis of the five-point scale for acute (Day 1) and overall (Day 4) gastric submucosal hemorrhages showed that every aspirin/guar formulation resulted in significantly lower scores for gastric submucosal hemorrhages and overall gastric erosions than aspirin alone. See Table 6.

TABLE 6

P-Values For Acute And Overall Gastric Submucosal Hemorrhages

| Treatment comparison | Acute p-value | Overall p-value |
|---|---|---|
| Aspirin vs. aspirin/0.1% guar | 0.0079 | 0.0337 |
| Aspirin vs. aspirin/0.6% guar | 0.0035 | 0.0204 |
| Aspirin vs. aspirin/1.4% guar | 0.0017 | 0.0031 |

Very few subjects had acute (Day 1) gastric erosions, so no treatment differences were found. The results for overall gastric erosions, however, showed that every aspirin/guar formulation resulted in significantly lower scores for overall gastric erosions than aspirin alone, as shown by Table 7.

TABLE 7

P-values For Acute and Overall Gastric Erosions

| Treatment comparison | Acute p-value | Overall p-value |
|---|---|---|
| Aspirin vs. aspirin/0.1% guar | 0.1554 | 0.0098 |
| Aspirin vs. aspirin/0.6% guar | 0.1554 | 0.0005 |
| Aspirin vs. aspirin/1.4% guar | 0.1156 | 0.0010 |

Few of the subjects experienced either hemorrhagic or erosive tissue damage in the duodenum. Consequently, endoscopy results for acute and overall duodenal submucosal hemorrhages and erosions showed no significant difference among treatments.

Results based on the presence vs. absence of gastrointestinal irritation (any irritation vs. no irritation) revealed differences, but no significant differences, among treatment groups, although at Day 1, the aspirin vs. aspirin/1.4% guar comparison demonstrated borderline significant (p=0.074).

Analysis of the presence vs. absence of damage showed a significant decrease in the presence of acute gastric submucosal hemorrhages with increasing guar concentration (p=0.013). The aspirin/1.4% guar formulation resulted in significantly fewer acute gastric submucosal hemorrhages than aspirin alone (p=0.012). The presence vs. absence analysis also showed a significant decrease in the presence of acute gastric erosions with increasing guar concentration (p=0.035). The aspirin/1.4% guar formulation resulted in significantly fewer acute gastric erosions than aspirin alone (p=0.032).

Exploratory analysis of severe vs. nonsevere tissue damage revealed that, at Day 1, all aspirin/guar groups demonstrated significantly less severe gastric hemorrhages than the aspirin-only group. Few subjects had gastric erosions at Day 1, so no differences among treatment groups were found. At Day 4, the aspirin/0.6% guar and aspirin/1.4% guar groups had significantly less severe gastric hemorrhages and erosions than the aspirin-only group.

From the above study it is concluded that:

1. The aspirin/guar formulations demonstrated markedly lower degrees of acute and overall gastric irritancy compared with aspirin alone.
2. As guar concentration increased, gastric erosions and submucosal hemorrhages significantly decreased.
3. Exploratory analyses revealed that the aspirin/0.6% guar and aspirin/1.4% guar groups demonstrated significantly lower severity of gastric hemorrhages and erosions than the aspirin-only group at both Days 1 and 4.
4. The rate and extent of aspirin absorption for the aspirin/guar formulations were similar to that of aspirin alone.

5. The aspirin/guar formulations resulted in mild to moderately severe, transient, loose stools (known to result from high fiber consumption).
6. The aspirin/guar formulations have an improved benefit/risk profile compared with aspirin alone.

EXAMPLE 3

This example provides representative compositions of this invention that contain a hydrocolloid from higher plants (guar gum) in a mucosally protective amount, a NSAID (aspirin-ASA), and other excipients. To be most effective the composition should have a disintegration time (DT) of less than about 5 minutes (preferably less than about 2 minutes and more preferably less than about 1 minutes) and a hardness rating of about 5 or more, preferably about 7 or more, most preferably about 9 or more.

The compositions were prepared having the components spelled out in Tables 8 and 9. In preparing the compositions, the aspirin was initially sieved through a 40 mesh screen. The powders were weighed to produce 30 gram batch sizes and mixed manually using geometric dilution. The tablets were compressed manually as well using a Stokes B-2 rotary tablet press. For the formulations that did not use 18% other excipients (CP-04-01, -13, and -14), the percentages are given in Table 8 and the difference was substituted with guar when necessary.

The formulations following CP-04-18 were made to determine if the overall weight of the aspirin tablets could be reduced. Additional excipients that were evaluated include Avicel PH302, Syloid and sodium lauryl sulfate. Tablets were made to either 1 gm, 950 mg, 900 mg, or 850 mg in size. All of the tablets were designed to contain 325 mg of ASA and 500 mg of guar in each. The individual ingredients and the tablet weights are summarized in Table 9. In formulations 18–21, the amount of guar and aspirin per tablet was kept constant, while the Crospovidone decreased. Other formulations included Crospovidone and Avicel combined with either Explotab (sodium starch glycolate) or Ac-Di-Sol® (sodium carboxymethylcellulose) at 2 and 4%.

Dry granulation was also evaluated for CP-04-19. Guar (Tic 822/A from the TIC Gum, Co.) and ASA portions were preweighed and mixed together. Large caplets of the mixture were compressed to a hardness averaging 10 Kp. Formulation CP-04-49 and CP-04-50 used a dry granulation of ASA and guar with and without crospovidone. The caplets were carefully crushed with a mortar and pestle and periodically sieved through an 18 and 40 mesh screen. The granules remaining on the 40 mesh screen were combined with the other ingredients.

Once the first group of formulations were made they were tested for disintegration times (DT) under static conditions. The tablets were placed in Bio-Dis dissolution vessels containing 100 ml USP simulated gastric fluid without enzymes (SGF) at 37° C. Without the dipping mechanism activated, the times for the tablets to disintegrate were recorded. Once a tablet appeared to be gone, the vessel was swirled to determine if a core was remaining. If a core was visible, the time was recorded once the core disappeared. Some formulations were also evaluated for disintegration times using the paddle method. The paddle speed was set to 50 rpm and the time to apparent disintegration was recorded. These were done in 500 ml of SGF at 37° C.

For the second group of formulations (Table 9), disintegration times were determined in cold and hot tap water (35–40° C.) under static conditions. This method was used for quick screening. The USP dissolution assay for aspirin tablets was run on some of the guar. The dissolution was performed in 500 ml of 0.05M acetate buffer. The medium was prepared by mixing 2.99 g of sodium acetate.

It should be noted that not all of the compositions in Table 8 have the favorable characteristics needed to be included in the compositions of this invention. For example, composition #CP-04-03, -04 and -05 exhibit disintegration times that are too high because the excipient is not sufficiently dispersion-enhancing. Under certain circumstances, e.g., combination with other components and in smaller amounts as in composition #CP-04-12, -22, -24, -26, -28, -30, -32, -34 and -36, these components can be used.

TABLE 8

The following formulations contain 32.5% ASA, 49.1% G3 Guar, 0.4% Mg. Stearate unless otherwise noted. Tablet weights were 1 gm. Disintegration times (DT) were determined in SGF at 35° C.

| Formu No. | Ingredients | hardness kp | DT (minutes) | Comments |
|---|---|---|---|---|
| CP-04-O1 | Guar alone | 7.9 | >30:00 | very little disintegration, worst case, at 30 minutes |
| CP-04-02 | 18%, Avicel PH200 | 10 | 4:05 | |
| CP-04-03 | 18% Encompress | 8.9 | >30:00 | about half disintegrated at 30 minutes |
| CP-04-04 | 18% Starch 1500 | <5 | >30:00 | very little disintegrated at 30 minutes |
| CP-04-05 | 18% Explotab | 5.2 | >30:00 | almost all disintegrated at 30 minutes |
| CP-04-06 | 18% Ac-Di-Sol | 5.7 | 2:50 | |
| CP-04-07 | 18% Crospovidone | 11.9 | 0:35 | 1. Swells rapidly to long gel mass (without stirring). 2. paddle: broke up rapidly, some chunks. 3. friability = 0.56% |
| CP-04-08 | 18% Dictose | 7.1 | 1:40 | paddle DT = 2:20 friability = 0.23% |
| CP-04-09 | 10% Avicel PH200 8% Ac-Di-Sol | 8.3 | 2:30 | paddle DT = 1:50 friability = 9.77% |

TABLE 8-continued

The following formulations contain 32.5% ASA, 49.1% G3 Guar, 0.4% Mg. Stearate unless otherwise noted. Tablet weights were 1 gm. Disintegration times (DT) were determined in SGF at 35° C.

| Formu No. | Ingredients | hardness kp | DT (minutes) | Comments |
|---|---|---|---|---|
| CP-04-10 | 10% Avicel PH200 8% Crospovidone | 9.9 | 1:20 | Swells similarly to 18% crospovidone. paddle: broke up rapidly |
| CP-04-11 | 10% Avicel PH200 8% Lactose | 10 | 3:50 | |
| CP-04-12 | 10% Avicel PH200 8% Explotab | 6.8 | 3:45 | |
| CP-04-13 | 9% Lactose | 7.4 | >10:00 | paddle DT = >5:00 slow to disintegrate |
| CP-04-14 | 27% Lactose | 12.5 | 2:40 | paddle DT = 2:10 |
| CP-04-15 | 14% Avicel PH200 4% Ac-Di-Sol | 9.4 | 2:30 | paddle DT = 2:05 friability = 0.68 % |
| CP-04-16 | 4% Avicel PH200 14% Ac-Di-Sol | 4.8 | 2:45 | paddle DT = 2:10 |
| CP-04-17 | 15% Avicel PH200 3% Syloid | 11.4 | 1:40 | very good flow friability = 0.09% |

TABLE 9

The following formulations contain 34.2% ASA, 52.6% G3 Guar, 0.4% Mg Stearate unless otherwise noted. Tablet weights were 950 mg. Disintegration times (DT) were determined in hot tap water (35–40° C).

| Formu No. | Ingredients | hardness kp | DT (minutes) | Comments |
|---|---|---|---|---|
| CP-04-18 | 32.5% 50% G3 guar 17.1% Crospovidone 0.4% Mg. Stearate | 9.5 | 0:20 | Tablet weight: 1 gm |
| CP-04-19 | 12.8% Crospovidone | 5.7 | 0:20 | Tablet weight: 950 mg |
| CP-04-20 | 36.1% ASA 55.6% G3 guar 7.9% Crospovidone 0.4% Mg. Stearate | 5.2 | 0:25 | Tablet weight: 900 mg |
| CP-04-21 | 38.2% ASA 58.5% G3 guar 2.5% crospovidone 0.4% Mg Stearate | 5.2 | 2:00 | Tablet weight: 850 mg |
| CP-04-22 | 10.8% Crospovidone 2% Explotab | 10.2 | 1:20 | |
| CP-04-23 | 10.8% Crospovidone 2% Ac-Di-sol | 10.3 | 1:00 | |
| CP-04-24 | 36.1% ASA 55.6% G3 guar 5.9% Crospovidone 2% Explotab | 6.9 | >2:00 | Tablet weight: 900 mg |
| CP-04-25 | 36.1% ASA 55.6% G3 guar 5.9% Crospovidone 2% Ac-Di-Sol | 7.5 | 1:20 | Tablet weight: 900 mg |
| CP-04-26 | 8.8% Crospovidone 4% Explotab | 6.5 | 1:05 | |
| CP-04-27 | 8.8% Crospovidone 4% Ac-Di-Sol | 8.0 | 0:55 | Friability = 0.29% |
| CP-04-28 | 3.9% Crospovidone 4% Explotab | 6.2 | >2:00 | Tablet weight: 900 mg |
| CP-04-29 | 3.9% Crospovidone 4% Ac-Di-Sol | 5.9 | 1:15 | Tablet weight: 900 mg |
| CP-04-30 | 10.8% Avicel PH200 2% Explotab | 9.0 | >2:00 | ~50% remaining |
| CP-04-31 | 10.8% Avicel PH200 2% Ac-Di-Sol | 8.6 | >2:00 | ~20% remaining |
| CP-04-32 | 5.9% Avicel PH200 2% Explotab | 7.2 | >2:00 | Tablet weight: 900 mg ~80% remaining |
| CP-04-33 | 5.9% Avicel PH200 2% Ac-Di-Sol | 7.2 | >2:00 | Tablet weight: 900 mg ~30% remaining |
| CP-04-34 | 8.8% Avicel PH200 4% Explotab | 7.5 | >2:00 | ~60% remaining |

TABLE 9-continued

The following formulations contain 34.2% ASA, 52.6% G3 Guar, 0.4% Mg Stearate unless otherwise noted. Tablet weights were 950 mg. Disintegration times (DT) were determined in hot tap water (35–40° C).

| Formu No. | Ingredients | hardness kp | DT (minutes) | Comments |
|---|---|---|---|---|
| CP-04-35 | 8.8% Avicel PH200<br>4% Ac-Di-Sol | 8.4 | >2:00 | ~20% remaining |
| CP-04-36 | 3.9% Avicel PH200<br>4% Explotab | 7.0 | >2:00 | Tablet weight: 900 mg<br>~80% remaining |
| CP-04-37 | 3.9% Avicel PH200<br>4% Ac-Di-Sol | 6.6 | >2:00 | Tablet weight: 900 mg<br>~15% remaining |
| CP-04-38 | 9.96% Avicel PH200<br>2.84% Ac-Di-Sol | 6.9 | 1:40 | |
| CP-04-39 | 9.76% Avicel PH200<br>2.79% Ac-Di-Sol<br>0.25% Syloid | 9.8 | 1:25 | |
| CP-04-40 | 8.3% Crospovidone<br>4.0% Avicel PH200<br>0.5% Syloid | 10.9 | 0:55 | |
| CP-04-41 | 8.3% Avicel PH200<br>4.0% Ac-Di-Sol<br>0.5% Syloid | 10.3 | 1:10 | Friability = 0.27%<br>USP Dissolution = 83.0% |
| CP-04-42 | 8.8% Crospovidone<br>4.0% Avicel PH 200 | 5.9 | 0:35 | |
| CP-04-43 | 8.8% Crospovidone<br>4.0% Avicel PH 302 | 6.4 | 0:40 | |
| CP-04-44 | 10% Avicel PH 302<br>2.8% Ac-Di-Sol | 7.1 | 1:00 | |
| CP-04-45 | 10.8% Avicel PH200<br>2.0% Sodium Lauryl Sulfate | 5.8 | 1:30 | |
| CP-04-46 | 1% Guar G3<br>(lot A3335D)<br>2% ASA<br>0.1% Tween 80<br>in sterile water | | | Suspension for Rat study |
| CP-04-47 | 1% purified guar<br>(lot: A3335D)<br>2% ASA<br>0.1% Tween 80<br>in sterile water | | | Suspension for Rat study |
| CP-04-48 | 9.5% Avicel PH302<br>0.5% Syloid<br>2.8% Ac-Di-Sol | 6.8 | 1:50 | friability = 0.69% |
| CP-04-49 | 52.6% Tic Guar 822A<br>12.8% Crospovidone | 5.3 | | ASA + guar + crospovidone dry granulated.<br>USP Dissolution = 83.4% |
| CP-04-50 | 52.6% Tic Guar 822A<br>12.8% Crospovidone | 10.3 | | ASA + guar dry granulated<br>USP Dissolution = 95.2% |
| CP-04-51 | 8.3% Crospovidone<br>4.0% Ac-Di-Sol<br>0.5% Syloid | 13.2 | 1:30 | Friabliity = 0.21%<br>USP Dissolution = 82.8% |
| CP-04-52 | 40.0% G3 guar<br>43.3% ASA<br>0.51% Mg Stearate<br>10.5% Avicel PH200<br>5.1% Ac-Di-Sol<br>4.75% Syloid | 6.9 | 0:32 | Tablet weight = 750 mg<br>Friability = 0.31% |
| CP-04-53 | 40.0% G3 guar<br>43.3% ASA<br>0.51% Mg Stearate<br>10.5% Crospovidone<br>5.1% Ac-Di-Sol<br>4.75% Syloid | 7.6 | 0:30 | Tablet weight = 750 mg<br>Friability = 0.20% |
| CP-04-54 | 41.7% G3 guar<br>45.1% ASA<br>0.4% Mg Stearate<br>8.3% Avicel PH200<br>4.0% Ac-Di-Sol<br>0.5% Syloid | 5.9 | 0:38 | Tablet weight = 720 mg<br>Friability = 0.35% |
| CP-04-55 | 41.7% G3 guar<br>45.1% ASA<br>0.4% Mg Stearate<br>8.3% Crospovidone<br>4.0% Ac-Di-Sol<br>0.5% Syloid | 6.2 | 0:20 | Tablet weight = 720 mg<br>Friability = 0.24% |

TABLE 9-continued

The following formulations contain 34.2% ASA, 52.6% G3 Guar, 0.4% Mg Stearate unless otherwise noted. Tablet weights were 950 mg. Disintegration times (DT) were determined in hot tap water (35–40° C).

| Formu No. | Ingredients | hardness kp | DT (minutes) | Comments |
|---|---|---|---|---|
| CP-04-56 | 8.3% Avicel PH200<br>4.5% Ac-Di-Sol<br>0.5% Syloid<br>0.4% Stearic Acid<br>NO Mg Stearate | 9.3 | 1:50 | Tablet weight = 750 mg<br>Friability = 0.11% (using only 5 tablets) |

EXAMPLE 4

This example shows the mucosal protective effect of a hydrocolloid gum obtainable from higher plants (guar gum) in an NSAID (ketoprofen) formulation and is similar to the tests done in Example 1.

In this example a dose of ketoprofen (100 mg/kg) was administered to rats to induce gastric damage and guar gum was coadministered to determine its effect. Both the ketoprofen and guar gum were administered as an aqueous mixture.

Seventy-five male Wistar rats each approximately 6 weeks of age and ranging in weight from 206 g to 233 g were housed 5 to a cage in suspended polypropylene cages with wire grid floors. The rats had access to tap water and were fed a standard certified laboratory rodent diet (RM1(E) SQC), ad libitum. Lighting in the animal room was controlled to give 12 hours light (0700–1900 hours) and 12 hours dark each day. The room temperature and relative humidity controls were set at 21° C.±3° C. and 50% ±15% respectively.

After an acclimatization period of 3 days following the day of arrival, the animals were randomized into groups according to bodyweight using random numbers tables so that the group mean bodyweights were approximately equal. Including the day of randomization, there were a further 3 days of acclimatization prior to dosing. Within each case, each animal was individually identified by tail marking.

The dose formulations were prepared on the day of the test by suspending Ketoprofen in 0.1% TWEEN 80. Guar gum was formulated in a ketoprofen suspension by vigorous stirring for 1 minute to achieve the required concentrations. Preparation and dosing were organized such that dosing of all animals within a treatment group was completed within three minutes of preparing the formulation. The rats were fasted for approximately 18 hours prior to the test; water was available ad libitam. During this time the rats were housed singly in a room maintained at a temperature of approximately 16° C.

On the day of the test the rats were orally dosed with either vehicle or test article at a constant dose volume of 10 ml/kg, according to the following treatment table:

| Group | Oral Treatment | Dose (mg/kg) |
|---|---|---|
| 1 | Vehicle (0% w/w) | — |
| 2 | Ketoprofen | 100 |
| 3 | Ketoprofen + Guar Gum 0.1% | 100 |
| 4 | Ketoprofen + Guar Gum 1.0% | 100 |
| 5 | Ketoprofen + Guar Gum 2.0% | 100 |

There were 15 rats in each treatment group.

Five hours after dosing, the rats were sacrificed by carbon dioxide asphyxiation and the stomachs removed. Each stomach was opened along the greater curvature and examined macroscopically for damage in the glandular portion; any damage was subjectively scored using the following system:

0=normal
1=overall reddening without sign of discrete hemorrhage
1=per small hemorrhage (>1 mm)
2=per large hemorrhage (>1 mm)
3=per small ulcer (>2 mm)
4=per large ulcer (>2 mm)
5=per perforated ulcer Where appropriate, the vehicle group and treatment groups were compared using analysis of variance or by using Student's t test.

The results set forth in Table 10 show that guar gum coadministered at a level of 1% and 2% produced about a 40% inhibition of ketoprofen-induced gastric damage (i.e. at a w:w ratio of Ketoprofen:guar of about 1:1 or 1:2).

TABLE 10

| Group | Oral Treatment | Dose (mg/kg) | Group mean score for gastric damage | % change from ketoprofen group (Group 2) |
|---|---|---|---|---|
| 1 | Vehicle | — | 0.1 | — |
| 2 | Ketoprofen | 100 | 13.1 | — |
| 3 | Ketoprofen + Guar Gum 0.1% | 100 + 0.1% | 15.3 | +16.8 |
| 4 | Ketoprofen + Guar Gum 1.0% | 100 + 1.0% | 7.9 | −39.7 |
| 5 | Ketoprofen + Guar Gum 2.0% | 100 + 2.0% | 7.9 | −39.7 |

EXAMPLE 5

By following the general principles set forth in Example 3 and elsewhere in the specification, similar compositions of this invention are prepared for other NSAIDs such as salicylic acid, aspirin, methyl salicylate, diflunisal, salsalate, phenylbutazone, oxyphenbutazone, apazone, mefenamic acid, meclofenamate sodium, indomethacin ibuprofen, naproxen naproxen sodium, fenoprofen, ketoprofen, flurbiprofen, piroxicam, diclofenac, etodolac, ketorolac, aceclofenac and nabumetone.

The subject matter claimed is:

1. A pharmaceutical composition suitable for oral delivery of a nonsteroidal anti-inflammatory dug (NSAID) as a unit dosage form capsule or tablet, which composition exhibits a mucosal protective effect and comprises
   (a) about 15% to about 90% by weight of a pharmaceutically-acceptable, powdered hydrocolloid gum obtainable from higher plants having a particle size distribution of between about 75 microns to about 300 microns;
   (b) about 5 to about 75% by weight of another dispersion-enhancing, pharmaceutically-acceptable excipient; and
   (c) a therapeutically-effective amount of the NSAID wherein said tablet or capsule has a disintegration time (DT) of less than about five minutes and a hardness rating of about five or more.

2. The composition of claim 1, wherein the powdered hydrocolloid gum is guar gum, gum tragacanth, locust bean gum, karaya gum, or a mixture thereof.

3. The composition of claim 2, wherein the gum is guar gum.

4. The composition of claim 1, wherein the NSAID is a salicylate, a pyrazolon, indomethacin, sulindac, a fenamate, tolmetin, a propionic acid derivative, or a pharmaceutically-acceptable salt thereof.

5. The composition of claim 4, wherein the NSAID is salacylic acid, aspirin, methyl salicylate, diflunisal, salsalate, phenylbutazone, indomethacin, oxyphenbutazone, apazone, mefenamic acid, meclofenamate sodium, ibuprofen, naproxen, naproxen sodium, fenoprofen, ketoprofen, fluribiprofen, piroxicam, diclofenac, etodolac, ketorolac, aceclofenac or nabumetone.

6. The composition of claim 5, wherein the composition comprises
   (a) about 20% to about 75% by weight of the hydrocolloid gum;
   (b) about 10% to about 50% by weight of the excipient; and
   (c) about 5% to about 45% by weight of the NSAID.

7. The composition of claim 1, wherein the gum is guar gum and the mucosal protective amount is about 240 milligrams or more.

8. The composition of claim 7, wherein the guar gum is present in an amount less that about a gram.

9. The composition of claim 1, wherein the NSAID is aspirin, naproxen, indomethacin, diclofenac or ketoprofen.

10. The composition of claim 9, wherein the NSAID is ketoprofen.

11. A method for reducing the gastric irritation effect of an NSAID after the oral administration of the NSAID to a subject in need thereof, which method comprises orally administering a unit dosage form capsule or tablet composition comprising
   (a) about 15% to about 90% by weight of a pharmaceutically-acceptable, powdered hydrocolloid gum obtainable from higher plants having a particle size distribution of between about 75 microns to about 300 microns;
   (b) about 5% to about 75% by weight of another dispersion-enhancing pharmaceutically-acceptable excipient; and
   (c) a therapeutically-effective amount of the NSAID, wherein said tablet or capsule has a disintegration time (DT) of less than about five minutes and a hardness rating of about five or more.

12. The method of claim 11, wherein the powdered hydrocolloid gum is guar gum, gum tragacanth, locust bean gum, karaya gum, or a mixture thereof.

13. The composition of claim 12, wherein the gum is guar gum.

14. The method of claim 13, where in the NSAID) is a salicylate, a pyrazolon, indomethacin, sulidac, a fenamate, tolmetin, a propionic acid derivative, or a pharmaceutically-acceptable salt thereof.

15. The method of claim 14, wherein the NSAID is salicylic acid, aspirin, methyl salicylatc, diflunisal, salsalate, phenylbutazone, indomethacin, oxyphenbutazone, apazonc, mefenamic acid, mcclofenamate sodium, ibuprofen, naproxen, naproxen sodium, fenoprofen, ketoprofen, fluribiprofcn, piroxicam, diclofenac, etodolac, ketorolac, aceclofenac or nabumetone.

16. The method of claim 15, wherein the composition comprises
   (a) about 20% to about 75% by weight of the hydrocolloid gum:
   (b) about 10% to about 50% by weight of the excipient; and
   (c) about 5% to about 45% by weight of the NSAID.

17. A process for preparing an orally-administrable unit dosage form capsule or tablet of an NSAID, which process comprises combining
   (a) about 15% to about 90% by weight of a pharmaceutically-acceptable, powdered hydrocolloid gum obtainable from higher plants having a particle size distribution of between about 75 microns and 300 microns;
   (b) about 5% to about 75% by weight of another dispersion-enhancing, pharmaceutically-acceptable excipient; and
   (c) a therapeutically-effective amount of the NSAID and forming a unit dosage form, wherein said tablet or capsule has a disintegration time (DT) of less than about five minutes and a hardness rating of about five or more.

18. The process of claim 17, wherein the powdered hydrocolloid gum is guar gum, gum tragacanth, locust bean gum, karaya gum, or a mixture thereof.

19. The process of claim 18, where the NSAID is saticylate, a pyrazolon, indomethacin, sulindac, a fenamate, tolmetin, a propionic acid derivative, or a pharmaceutically-acceptable salc thereof.

20. The process of claim 19, wherein the NSAID is salicylic acid, aspirin methyl salicylate, diflunisal, salsalate, phenylbutazone, indomethacin, oxyphenbutazone, apazone, mefenamic acid, meclofenamate sodium, ibuprofen, naproxen, naproxen sodium, fenoprofen, ketoprofen, fluribiprofen, piroxicam, diclofenac, etodolac, ketorolac, aceclofenac or nabumetone.

21. The process of claim 20, wherein the composition comprises
   (a) about 20% to about 75% by weight of the hydrocolloid gum;
   (b) about 10% to about 50% by weight of the excipient; and
   (c) about 5% to about 45% by weight of the NSAID.

* * * * *